Oct. 18, 1938. I. RINGDAHL Plant Pat. 295
ROSE
Filed Jan. 27, 1938
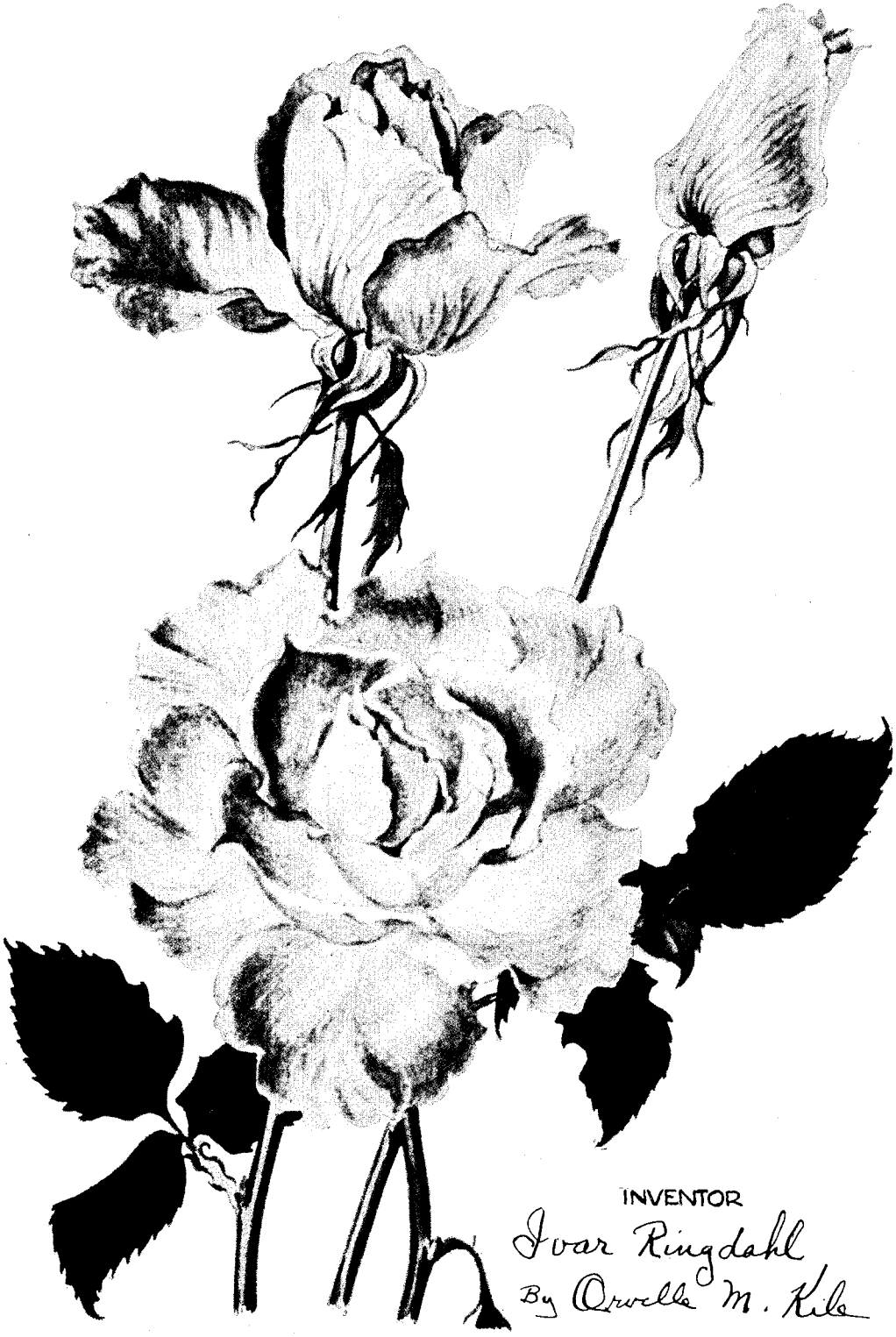
INVENTOR
Ivar Ringdahl
By Orville M. Kile
PLANT PATENT AGENT Patented Oct. 18, 1938

Plant Pat. 295

UNITED STATES PATENT OFFICE

235

ROSE

Ivar Ringdahl, Rome, N. Y.

Application January 27, 1938, Serial No. 187,329

1 Claim. (Cl. 47—61)

My present discovery relates to a new and distinct variety of rose plant of the hybrid tea class. It is a sport of Better Times and has many of the qualities of its parent plant, although it differs in several definite and important points. The novel qualities claimed have been observed through several asexually-produced generations and have been shown to be firmly established.

The accompanying illustration shows three specimens of the variety in varying stages of opening.

Following is a more complete description of this variety. Color plate references are to Ridgway's Color Standards and Nomenclature.

*The plant*

Growth:

Upright bush, attaining a height up to 4 feet. Very prolific. Practically free from blind wood.

Foliage:

Abundant. Thick and leathery.

*Color.*—Very dark green—the shade of Dusky Yellowish Green to Dull Blackish Green (Plate XLI) on upper surface, but with a waxy, glossy appearance. Under surface is dull and of a lighter, grayish green approximately Russian Green (Plate XLII). Most of the leaves have a bronzy cast on the under surface and some also on the upper surface although the latter is decidedly weaker.

*Leaflets.*—First leaf below peduncle is single and often irregularly shaped. Second leaf has three leaflets; others five to seven. The central, terminal leaflet averages 2 to 2¾ inches in length. Lateral leaflets are smaller. Leaflets have sharply and regularly serrated edges and are oval with sharp-pointed tip.

Stems:

Stout, stiff, long, Elm Green (Plate XVII). Thorns appear on lower part of stem but upper part is smooth. Thorns are sharp, pink, downward-pointing.

Stipules:

Long and wide, clinging close to petiole. Have sharp, short points which do not curve.

Rachis:

Heavy. Upper side grooved; lower side with several small, sharp thorns.

*The flower*

Bud:

Very long. Well-formed. Opens slowly and evenly.

*Color.*—Between Rose Red and Pomegranate Purple (Plate XII).

*Peduncle.*—Long and stiff, holding bloom erect. Smooth. Same color as the stem.

Blossom:

Borne singly.

*Size.*—Very large, often opening to a 5½ or 6 inch spread.

*Form.*—High centered, with outer petals remaining flat to form a frame about the center. This arrangement gives the appearance of a very full and large rose although its petalage is not great. After several days the center of the flower opens up to show the stamens and pistils which are numerous.

*Petalage.*—Usually 25 to 35 petals, varying with the season and other conditions. Occasionally there are as many as 50 petals.

*Petals.*—The outer petals are exceptionally large, averaging 2 to 2¼ inches in length and 2¼ to 2½ inches across on typical blossoms. Petals are broadly obovate in shape and do not quill or roll back. The inner petals are not so large and are narrower, being more nearly spatulate in shape. The petals are slightly crinkled and notched at the edges but the greater part is smooth and uncrinkled. Petals are of heavy substance. The upper surface is velvety and the under surface satiny.

*Color.*—Ridgway's Color Standards and Nomenclature does not give a color exactly like the color of this rose but the nearest falls between Tyrian Rose and Amaranth Purple (Plate XII). The under side of the petals is slightly lighter than the upper side but is of the same general tone. The color appears to be spread rather uniformly over the surface of the petals, giving the effect of a solid color. However, upon closer examination it is seen that the petals are slightly lighter toward the base. When the flower opens wide, a number of vertical white streaks are seen upon the inner petals. These streaks, of course, are not apparent in the earlier stages of opening. A particular feature of this rose is its constancy of color which fades or changes very little as it ages.

*Keeping qualities.*—Exceptionally good, keeping for several days before opening completely, and then lasting for several days more. There is very little change of the coloring as the flower ages.

*Fragrance.*—Fragance is particularly pronounced and lasting. However it is pleasing rather than strong.

*Sepals.*—Ordinarily sepals are 1½ to 2½ inches in length but sometimes two of the five tend to be foliaceous. Permanent. Curve backward.

*Reproductive organs*

Hips:
Small. Tapered. Smooth. Same color as peduncle.

Stamens:
Many. Arranged about ovary and attached at point where calyx turns backward.

Filaments:
Redish in color. Varying in length. Most of them have anthers.

Anthers:
Large. Yellow.

Pistils:
Many.

Styles:
Many. White. Bunched but each distinct. Fairly even in length.

Stigma:
White with reddish tinge on some of them.

Petaloids:
Between the pistils and the stamens which encircle the pistils, is a row of rudimentary petaloids which have the color of the pistils but are more fleshy and are usually curved and crumpled.

*Comparisons*

The varieties which most resemble this new variety are Better Times (its parent), Happy Days and Peerless, all of which are sports of Briarcliff. However, these varieties differ from my new variety in several important points, some of which are given as follows:

*Comparison with Better Times (Pl. Pat. No. 23)*

1. The color of the bloom is several shades darker and is more uniform in my new variety, and the base of the petals does not show a white portion as in Better Times.
2. Petals of my new variety are velvety on upper side and satiny on under side, while those of Better Times are merely silky on both surfaces.
3. The petals of the new variety do not curl backward or quill upon opening as do those of Better Times.
4. There are not as many petals in the new variety.
5. The outer petals of the new variety are considerably larger than those of Better Times. The inner petals are longer, making a higher-centered rose.
6. The new variety is a more prolific producer.
7. The new variety retains its color to a greater degree than does Better Times.
8. The new variety produces much less blind wood.
9. The under side of the leaf of the new variety is more inclined to be bronzy than is the Better Times variety.

*Comparison with Happy Days (Pl. Pat. No. 144)*

1. The color of the new variety is entirely different from that of Happy Days, and is much more evenly distributed.
2. The new variety has a much smaller number of petals than Happy Days.
3. The spread of blossoms of the new variety is greater although the petalage is smaller than that of Happy Days.

*Comparison with Peerless (Pl. Pat. No. 157)*

1. The blossom of the new variety is in an entirely different color range from that of Peerless.
2. The new variety has a slightly smaller average number of petals than the Peerless.
3. The sepals of the new variety are much longer and more foliaceous than those of Peerless.

Having thus disclosed my discovery, I claim:

The new and distinct variety of rose plant as shown and described, characterized particularly by its abundant dark foliage of heavy substance, its unusually long bud, and its prolific production of blooms of exceptionally good keeping qualities, lasting fragrance, distinctive permanent color between Tyrian Red and Amaranth Purple, and with petals of very large size.

IVAR RINGDAHL.